US00PP13146P2

(12) United States Plant Patent
Glancy

(10) Patent No.: US PP13,146 P2
(45) Date of Patent: Oct. 29, 2002

(54) PHALAENOPSIS PLANT NAMED (KEN PETERSON×MAMA CASS) 'PINE RIDGE #3'

(75) Inventor: Terry A. Glancy, Homestead, FL (US)

(73) Assignee: Twyford International Inc., Santa Paula, CA (US)

( * ) Notice: Subject to any disclaimer, the term of this patent is extended or adjusted under 35 U.S.C. 154(b) by 8 days.

(21) Appl. No.: 09/895,637

(22) Filed: Jun. 30, 2001

(51) Int. Cl.[7] ..... A01H 5/00
(52) U.S. Cl. ..... Plt./311
(58) Field of Search ..... Plt./311

*Primary Examiner*—Bruce R. Campell
*Assistant Examiner*—Susan B. McCormick

(74) *Attorney, Agent, or Firm*—C. A. Whealy

(57) ABSTRACT

A new and distinct Phalaenopsis Orchid plant named (Ken Peterson×Mama Cass) 'Pine Ridge #3' which produces numerous orange pink-colored flowers on sturdy, upright, and frequently branched racemes. The flowers are long lasting and of good substance. The flowers change color noticeably with age becoming pink tinged with yellow. The plants flower early in the season and have been observed to flower off-season. The foliage is dark green and glossy. Plants of the new cultivar grow very quickly to marketable size. The above features combined make the new cultivar particularly well-suited to commercial production and marketing practices.

2 Drawing Sheets

BACKGROUND OF THE INVENTION

The present invention comprises a new and distinct cultivar of Phalaenopsis Orchid, and hereinafter referred to by the cultivar name, (Ken Peterson×Mama Case) 'Pine Ridge #3'. The new cultivar may be marketed under the name Summer Beach.

Phalaenopsis comprises a genus of about 55 species of herbaceous perennials; many of which, or the hybrids thereof, are suitable for cultivation in the home or greenhouse. Phalaenopsis are predominantly epiphytic or rock-dwelling, and are native to tropical Asia, the Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

Phalaenopsis orchids, referred to as 'Moth Orchids' in the horticultural trade, are used as cut flowers for the florist trade, or sold as flowering potted plants for the home or interiorscape.

Phalaenopsis produce upright or pendent lateral flowering racemes, often with many showy flowers which open in succession beginning with the lowermost. The flowers possess three sepals, and three petals, the lateral ones are similar. The lowermost petal, called the labellum, is three-lobed and is often more brightly colored than the other flower segments. Flower colors include various shades of pink, white, yellow, and red-brown.

Phalaenopsis Orchids are typically propagated from seeds. Asexual propagation of Phalaenopsis is often done from off-shoots which frequently arise from the lower bracts of the inflorescence. The resulting plants are detached from the mother plant and planted in a suitable substrate. Phalaenopsis Orchids may also be asexually reproduced by tissue culture.

The new cultivar was discovered by the Inventor within the progeny of a cross of the parent plants listed below that was made in April, 1995. The new Cultivar was selected by the Inventor as a flowering plant in a controlled environment in Homestead, Fla. in February, 1997. Since January, 1998, asexual propagation by tissue culture in a laboratory in Sebring, Fla. has been used to increase the number of plants for evaluation and has demonstrated that the unique combination of characteristics as herein disclosed for the new cultivar are firmly fixed and are retained through successive generations of asexual reproduction.

SUMMARY OF THE INVENTION

The following traits have been repeatedly observed and are determined to be basic characteristics of new cultivar which in combination distinguish this Phalaenopsis as a new and distinct cultivar:

1. Flowers of the new cultivar are orange pink in base color, with a suffusion of pink at the base of the lateral petals. The labellum is multi-colored and variously marked with red, dark pink and yellow. The color of the flower changes noticeably with age becoming pink tinged with yellow.
2. Inflorescences of the new cultivar are tall, frequently branched, and sturdy with long lasting flowers with good substance.
3. Leaves of the new cultivar are elliptic to obovate in shape, very dark green, and glossy. The undersides of the leaves are flushed with dark purple.
4. Plants of new cultivar grow quickly, uniformly, and vigorously.
5. Plants of the new cultivar flower early, producing marketable flowering plants in about 11 months.
6. Plants of the new cultivar initiate flowers early in the fall, and flower in advance of the typical flowering season during the winter and early spring. Plants of the new cultivar have also been observed to flower during the summer.

Plants of the new cultivar have not been observed under all possible environmental conditions. The phenotype may vary significantly with variations in environment such as temperature, light intensity, and daylength, without however, any change in genotype.

Plants of the new cultivar differ primarily from plants of the parent cultivars in petal and sepal color. Plants of the new cultivar differ primarily from plants of the Phalaenopsis (Ken Peterson×Mama Cass) 'Pine Ridge #6', disclosed in U.S. Plant patent application Ser. No. 09/895,636, filed concurrently with this application, in petal and sepal color.

Perhaps the closest commercial comparison to the new cultivar can be made to seedling-derived Phalaenopsis Orchids which are heterogeneous genetically, and typically lack uniformity in growth vigor, plant growth habit, and flower quality. Since this reference point has inconsistent characteristics, a direct comparison for (Ken Peterson× Mama Cass) 'Pine Ridge #3' is not available. The new cultivar is a single genotype asexually-propagated via tissue culture; thus its combined horticultural characteristics listed above are uniform and predictable.

BRIEF DESCRIPTION OF THE PHOTOGRAPHS

Colors in the photographs may appear different from the color values that appear in the detailed botanical description which more accurately describe the new cultivar.

The photograph on the first sheet comprises a side perspective view of three typical flowering plants of the new cultivar grown in 10-cm containers.

The photograph on the second sheet comprises a close-up view of a typical inflorescence of the new cultivar. The plant depicted in these photographs were grown for about 11 months under appropriate growing conditions.

DETAILED BOTANICAL DESCRIPTION

All color references are measured against The Royal Horticultural Society Colour Chart, (1995 edition). Colors and numerical measurements are approximate as plant growth and development depends on horticultural practices such as light level, temperature, water status and fertilization rate, among others, without, however any change in genotype.

Plants used for the description were about 11 months old and grown in 10-cm containers in Homestead, Fla., in a polyethylene-covered greenhouse with day temperatures about 78 to 96° F., night temperatures about 60 to 82° F., and light levels below 1,000 foot-candles. Information for this description was taken during the winter, 2001.

Botanical classification: Phalaenopsis (Ken Peterson×Mama Cass) cultivar Pine Ridge #3.

Parentage: Seedling selected from a cross of the following:

*Seed parent*.—Phalaenopsis cultivar Ken Peterson.

*Pollen parent*.—Phalaenopsis cultivar Mama Cass. The cross listed above has since been recorded by The Royal Horticultural Society under the name Ken Peterson×Mama Cass.

Propagation:

*Type*.—Asexual propagation by tissue culture.

*Time to initiate and elongate roots*.—Summer: About 28 days at 82 to 96° F. Winter: About 42 days at 60 to 78° F.

*Time to produce a fully rooted young plant*.—Summer: About 120 days at 82 to 96° F. Winter: About 180 days at 60 to 78° F.

*Root description*.—Very thick, fleshy, and greenish white in color.

*Plant description*.—Under appropriate growing conditions, plants of the new cultivar attain a mature size of approximately 10 to 17 cm in height (top of leaf plane) and about 30 to 37 cm in width.

Leaf description:

*Form*.—Leaves are elliptic to obovate with acute to obtuse apex and cuneate base; margins are entire. The leaf blade is flat or slightly folded upward from the midrib. Leaves are flat or curved downward towards the apex. The leaf margin is flat or cupped downward. The upper leaf surface is glossy; young leaves are glossier than fully expanded leaves; the lower leaf surface is dull. Leaves are leathery, thick and glabrous.

*Size*.—Leaf blades of a mature-sized plant are about 20 cm in length and about 8.5 cm in width.

*Veins*.—Veins are sunken within the lamina.

*Color*.—Adaxial surface: Darker than, but closest to 137A. Young leaves flushed with 187A along margin towards leaf base. Abaxial surface: Darker than, but closest to 147B tinged with 187A particularly towards the base and margin.

Flower/inflorescence description:

*Description*.—The sepals and petals are orange pink in base color, with a suffusion of pink at the base of the lateral petals. The bases of the sepals and lateral petals are marked with a concentric array of darker orange pink speckles. The sepals are elliptic in shape, the dorsal sepal has a retuse apex, and the lower sepals have acute apices. The lateral petals are broadly ovate with rounded apices. The sepals and petals are flat or slightly cupped. The labellum is deeply three-lobed with two prominent callosities at the central junction of the lateral lobes and base of the midlobe. The lateral lobes of the labellum fold upward about the column, the midlobe extends forward and is terminated by two short appendages at the apex. The lateral lobes of the labellum are obvate in shape, the midlobe is triangular. The labellum is multi-colored and variously marked with red, dark pink and yellow at the junction of the segments. The callosities are yellow with red-purple spots and stripes.

*Dimensions*.—Flower: About 5.9 to 6.3 cm wide, and about 5.1 to 5.6 cm in height. Sepals: About 2.9 to 3.2 cm long, and about 2.3 to 2.5 cm wide. Petals: About 2.9 cm long, and about 2.9 to 3.1 cm wide. Labellum: About 2.2 cm long and about 1.8 cm wide (not flattened).

*Coloration*.—Sepals: Front surface: Lighter than but closest to 180D, flushed with 174C when newly open. Towards apices, 20D; base of sepals speckled and marked with 180C. With age, fading to 19Cflushed with 54C to 54D. Reverse surface: 174B to 174C tinged with 162D. With age, fading to 159B tinged with 65D. Lateral Petals: Front surface: Lighter than, but closest to 180D, flushed with 174C when newly open. Towards apices, 20D; base of sepals speckled and marked with 180C and 82D. With age, fading to 19C, flushed with 54C to 54D; base of sepals speckled and marked with 82D. Reverse surface: 174D tinged with 162C. Base of petal tinged with 82D. With age, fading to 159C tinged with 65D. Labellum: Front surface: Lateral Lobes: Ground color, 158D, nearly covered with speckles and spots of 180A to 180B. With age, fading to 158D with fine speckles of 184A. Midlobe:

184 A. With age, fading to 184B to 64D. Callosities: Yellow, 13C, with fine speckles of 185A. Reverse surface: Lateral lobes: White, 155D, with 60A. With age, fading to 155D with 184C. Midlobe: 184A to 77C. With age, fading to 184B to 184C to 77C.

*Raceme*.—Dimension: The raceme is about 60 cm from base to tip, and about 5 mm in diameter at its midpoint. About 10 to 15 flowers are produced on each raceme. One or two branch spikes, containing 2 to 5 flowers/buds are typically produced. The raceme is 200C tinged with 147A in color.

*Quantity of flowers and time to flower*.—Flowering starts about 3 to 6 months after planting 12-week old liners; first time flowering plants produce about 3 to 4 flowers per raceme.

*Flower longevity*.—Individual flowers maintain good substance and coloration for about two months on the plant. Inflorescences are in flower for about 3 to 5 months on the plant.

*Natural flowering season*.—Plants of the new cultivar initiate flowers early in the fall, and flower in advance of the typical flowering season during the winter and early spring. Plants of the new cultivar have also been observed to flower during the summer.

Reproductive organs: The stamens, style and stigmas are fused into a single short structure called the column, possessing one terminal anther with pollen grains united into a pollinia, which are covered by an anther cap. The stigma is located under the column behind the pollinia. Ovary inferior, three carpels present.

*Column*.—The column is about 1.1 cm long, about 5 mm wide, and 155D tinged with 82C in color.

*Pollinia*.—Two oval masses of pollen present, about 1 mm in diameter, and 23A in color.

*Stigma*.—Concave, sticky rectangular area, under column, about 5 mm by 4 mm in size, and 155D in color.

*Ovary*.—About 1.2 cm long, about 2.5 mm diameter, and 186D in color.

*Pedicel*.—About 1.9 cm long, about 3 mm in diameter, and 200C overlain with 147B in color.

*Seed*.—Seed production has not been observed.

Temperature tolerance: Plants of the new cultivar have been observed to tolerate temperatures from 45 to 105° F.

Disease/pest resistance: Plants of the new cultivar have not been observed to be resistant to pathogens or pests common to Phalaenopsis Orchids.

General observations: Plants of (Ken Peterson×Mama Cass) 'Pine Ridge #3' produce numerous orange pink-colored flowers on tall, sturdy, upright, and frequently branched racemes. The flowers are long lasting and of good substance. The flowers change color noticeably with age becoming pink tinged with yellow. The plants flower early in the season and have been observed to flower off-season. The foliage is dark green and glossy. The plant grows very quickly to marketable size.

It is claimed:

1. A new and distinct cultivar of Phalaenopsis Orchid plant named (Ken Peterson×Mama Cass) 'Pine Ridge #3', as illustrated and described.

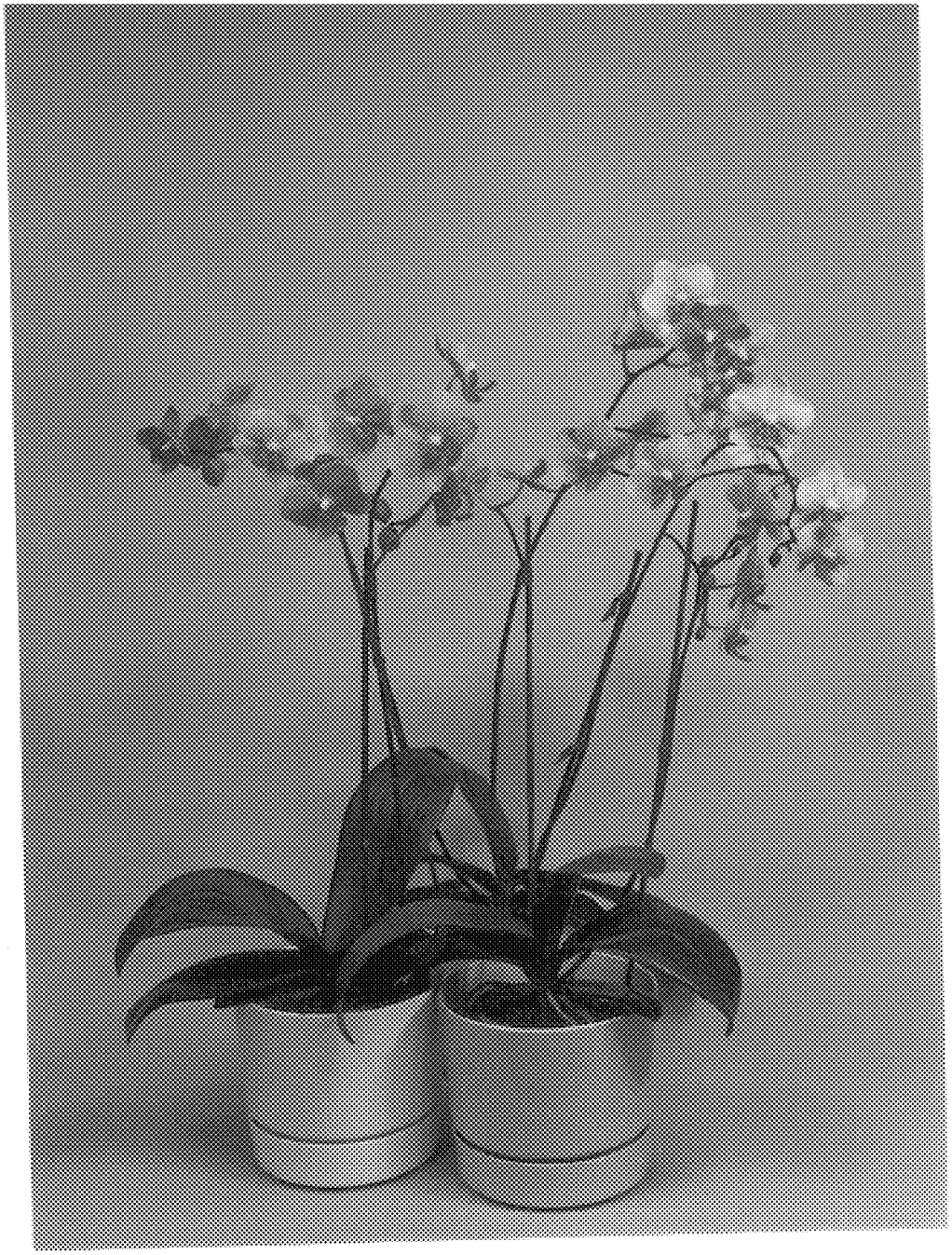

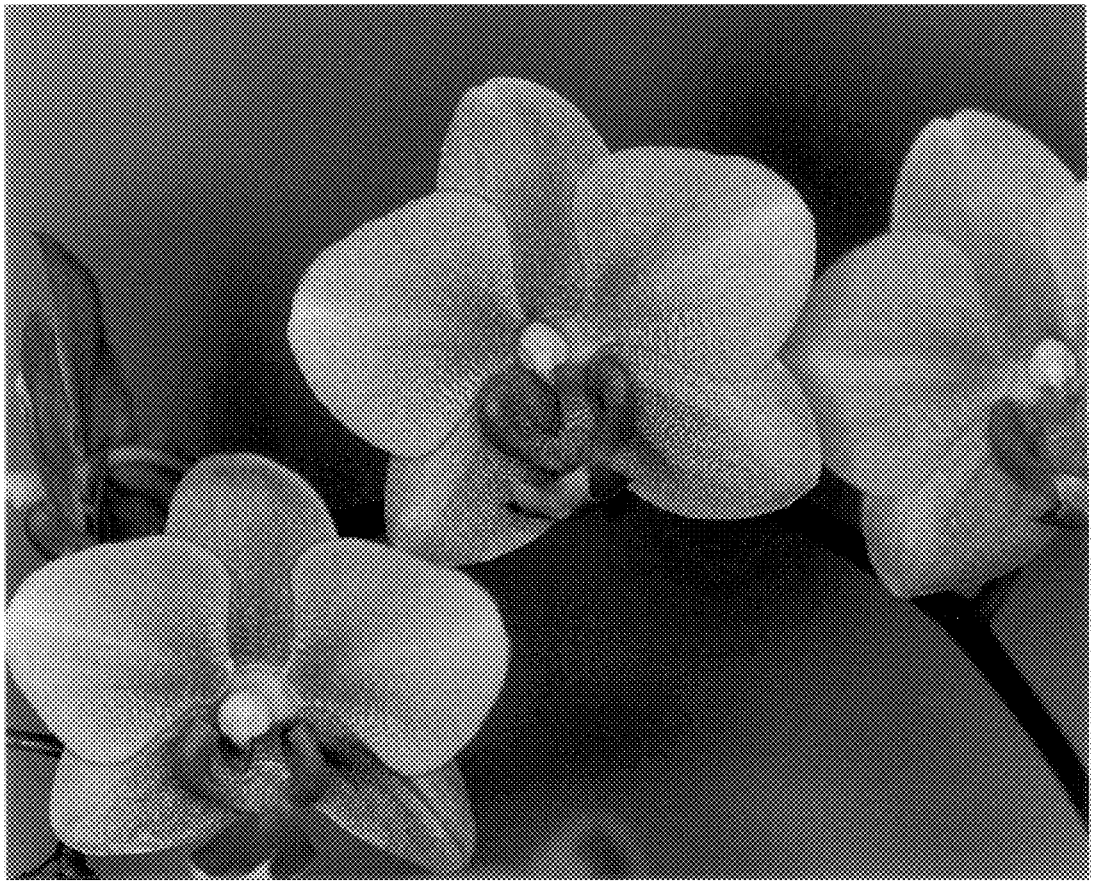

* * * * *